US010656291B2

(12) United States Patent
Grobshtein et al.

(10) Patent No.: US 10,656,291 B2
(45) Date of Patent: May 19, 2020

(54) SYSTEMS AND METHODS FOR IMAGE QUALITY ENHANCEMENT FOR OUT OF FOCUS REGIONS FOR MULTI-HEAD CAMERA

(71) Applicant: General Electric Company, Schenectady, NY (US)

(72) Inventors: Yariv Grobshtein, Haifa (IL); Michal Merman, Nesher (IL)

(73) Assignee: General Electric Company, Schenectady, NY (US)

( * ) Notice: Subject to any disclaimer, the term of this patent is extended or adjusted under 35 U.S.C. 154(b) by 164 days.

(21) Appl. No.: 15/452,305

(22) Filed: Mar. 7, 2017

(65) Prior Publication Data

US 2018/0259659 A1 Sep. 13, 2018

(51) Int. Cl.
| | | |
|---|---|---|
| *G01T 1/29* | (2006.01) | |
| *G06T 11/00* | (2006.01) | |
| *G06T 5/00* | (2006.01) | |
| *A61B 6/00* | (2006.01) | |
| *A61B 6/03* | (2006.01) | |

(52) U.S. Cl.
CPC ............ *G01T 1/2985* (2013.01); *A61B 6/037* (2013.01); *A61B 6/501* (2013.01); *A61B 6/5205* (2013.01); *A61B 6/54* (2013.01); *G06T 5/002* (2013.01); *G06T 11/003* (2013.01); *G06T 11/005* (2013.01); *G06T 11/006* (2013.01); *G06T 2211/424* (2013.01)

(58) Field of Classification Search
CPC ....... G01T 7/00; G01T 1/1642; G01T 1/2985; G06T 5/002; G06T 11/003; G06T 11/005
See application file for complete search history.

(56) References Cited

U.S. PATENT DOCUMENTS

| | | | | |
|---|---|---|---|---|
| 5,821,541 A | * | 10/1998 | Tumer | G01T 1/006 250/370.09 |
| 5,853,370 A | * | 12/1998 | Chance | A61B 5/0073 600/473 |
| 8,492,725 B2 | | 7/2013 | Zilberstein et al. | |
| 2003/0031289 A1 | * | 2/2003 | Hsieh | A61B 6/032 378/4 |

(Continued)

*Primary Examiner* — David P Porta
*Assistant Examiner* — Jeremy S Valentiner
(74) *Attorney, Agent, or Firm* — Dean D. Small; The Small Patent Law Group, LLC

(57) ABSTRACT

A nuclear medicine (NM) multi-head imaging system is provided that includes a gantry, plural detector units mounted to the gantry, and at least one processor. Each detector unit defines a detector unit position and corresponding view oriented toward a center of the bore, and is configured to acquire imaging information over a sweep range. The at least one processor is operably coupled to at least one of the detector units, and is configured to acquire, via the detector units, imaging information. The imaging information includes focused imaging information corresponding to a focused region and background imaging information corresponding to surrounding tissue of the focused region. The at least one processor is also configured to reconstruct an image using the focused imaging information and the background imaging information using a first reconstruction technique for the focused imaging information and a different, second reconstruction technique for the background imaging information.

14 Claims, 8 Drawing Sheets

(56) References Cited

U.S. PATENT DOCUMENTS

| | | | |
|---|---|---|---|
| 2005/0082486 A1* | 4/2005 | Schlyer | A61B 6/037 250/363.01 |
| 2009/0116619 A1* | 5/2009 | Chapman | G01J 1/04 378/145 |
| 2012/0063665 A1* | 3/2012 | Wang | A61B 5/0066 382/134 |
| 2012/0265050 A1* | 10/2012 | Wang | A61B 5/055 600/411 |
| 2014/0126793 A1 | 5/2014 | Ahn et al. | |
| 2014/0126794 A1* | 5/2014 | Ahn | G06T 11/008 382/131 |
| 2014/0211157 A1* | 7/2014 | Nakahara | A61B 3/102 351/206 |
| 2016/0055658 A1* | 2/2016 | Liang | G06T 11/006 382/131 |
| 2017/0000448 A1* | 1/2017 | Hefetz | A61B 6/037 |
| 2017/0014096 A1* | 1/2017 | Bouhnik | A61B 6/545 |
| 2018/0103918 A1* | 4/2018 | Bagamery | A61B 6/037 |

* cited by examiner

SYSTEMS AND METHODS FOR IMAGE QUALITY ENHANCEMENT FOR OUT OF FOCUS REGIONS FOR MULTI-HEAD CAMERA

BACKGROUND

The subject matter disclosed herein relates generally to medical imaging systems, and more particularly to radiation detection systems.

In nuclear medicine (NM) imaging, such as single photon emission computed tomography (SPECT) or positron emission tomography (PET) imaging, radiopharmaceuticals are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

An NM imaging system may be configured as a multi-head imaging system having several individual detectors distributed about the gantry. Each detector may pivot or sweep to provide a range over which the detector may acquire information that is larger than a stationary field of view of the detector. Focus-based acquisition may improve image quality in a focused region, but image quality in an out-of-focus region may be significantly degraded, which may pose problems in clinical protocols that use both regions for clinical analysis and diagnosis.

BRIEF DESCRIPTION

In accordance with an embodiment, a nuclear medicine (NM) multi-head imaging system is provided, that includes a gantry, plural detector units mounted to the gantry, and at least one processor. The gantry defines a bore configured to accept an object to be imaged. The detector units are mounted to the gantry. Each detector unit defines a detector unit position and corresponding view oriented toward a center of the bore, and is configured to acquire imaging information over a sweep range corresponding to the corresponding view. The at least one processor is operably coupled to at least one of the detector units, and is configured to acquire, via the detector units, imaging information. The imaging information includes focused imaging information corresponding to a focused region and background imaging information corresponding to tissues surrounding the focused region. The at least one processor is also configured to reconstruct an image using the focused imaging information and the background imaging information using a first reconstruction technique for the focused imaging information and a different, second reconstruction technique for the background imaging information.

In accordance with another embodiment, a method includes acquiring, via plural detector units, imaging information comprising focused imaging information corresponding to a focused region and background imaging information corresponding to tissues surrounding the focused region. Each detector unit defines a detector view and has a sweep range. The method also includes reconstructing an image using the focused imaging information and the background imaging information using a first reconstruction technique for the focused imaging information and a different, second reconstruction technique for the background imaging information.

In accordance with another embodiment, a method includes independently determining, for each detector unit of a system, a percentage of focused time for acquiring focused imaging information corresponding to a focused region, and a percentage of background time for acquiring background imaging information corresponding to tissues surrounding the focused region. The system includes plural detector units each defining a detector view and having a sweep range. The percentages are determined based on at least one of detector proximity to the focused region, relative angular span of the focused region relative to total detector angular field of view, or anticipated attenuation qualities in a detector field of view. The method also includes acquiring the imaging information using the determined percentages of focused time and background time.

DETAILED DESCRIPTION

Figure 1:
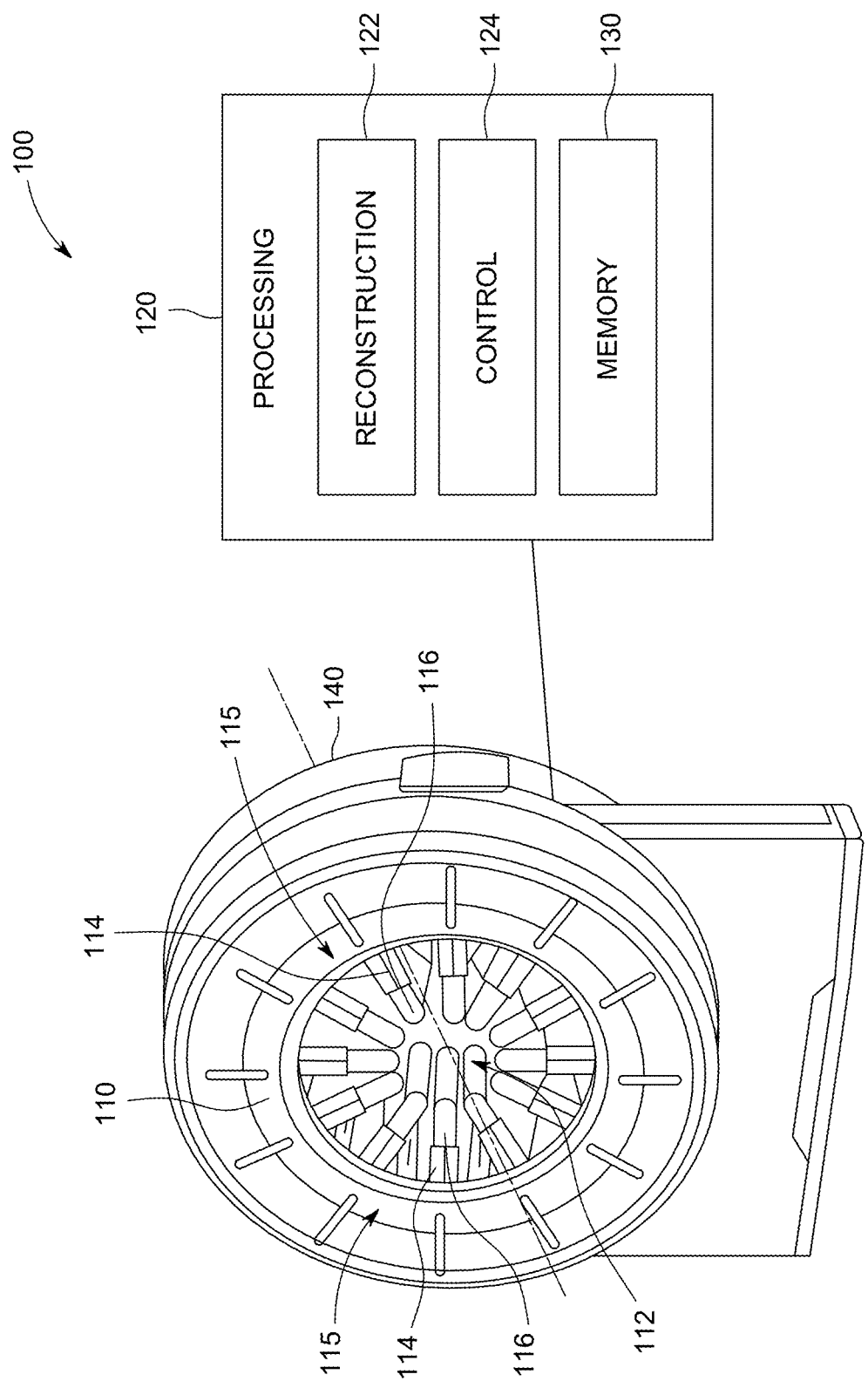
FIG. 1 provides a schematic view of a nuclear medicine (NM) imaging system according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for improving image quality for focused scans for NM imaging systems including at least one detector that sweeps over a range during image acquisition.

In focused scans, the acquisition of imaging information may be understood as non-uniform, in that the detectors spend more time focused on a specific area (or areas) of an object relative to surrounding tissue or background regions. While such an approach improves image quality of a focused area, image quality of other areas may be significantly degraded. Various embodiments of the present disclosure provide systems and/or methods to improve image quality of out-of-focus regions, which is useful in certain clinical protocols. It may be noted that various embodiments need not necessarily be limited to time-based focusing. For example, non-uniform acquisition in an angular domain may be utilized additionally or alternatively to the employment of non-uniform time for focused acquisition. For example, embodiments using beta masks or reprojection techniques as discussed herein are not limited to time focus. As used herein, non-uniform acquisition in the angular domain may be understood as applying to acquisition for which more angular projections are acquired in a focused region (or regions) compared with a background region (or regions). It may be noted that the acquisition time for each angular view may be the same for all angular views, or may be different. Accordingly, focusing may be achieved in a time domain, in an angular domain, or via a combination of the two.

Various embodiments provide or utilize reconstruction and/or acquisition techniques for improving image quality of out-of-focus or background regions. In some embodiments, different reconstruction techniques are employed for imaging information from a focused region and for imaging information from a background or out-of-focus region, for example to account for different quantities of available imaging information. It may be noted that, as used herein, in various embodiments, a focused region may include one or more distinct portions (or multiple different regions). For example, in some embodiments there are two or more separate or distinct focused regions. As one example, in some embodiments, two kidneys may define focused regions, with each kidney a separate focus region, while the spaces before, after, and between the kidneys are out-of-focus or background regions.

For example, in some embodiments regularized reconstruction is employed with non-uniform regularization (or penalty weights). For instance, different weights are applied regionally or locally (e.g., a first weight used for the focused region and a different, second weight used for the background or out-of-focus region). As another example, in some embodiments, computed re-projected views for an out-of-focus region are generated and used in combination with original measured projection data for a focused region to provide a combined reconstruction.

As one more example, in some embodiments, non-uniform scan patterns (e.g., independently determined for each detector) are used to acquire the imaging information. Each column or detector unit may acquire imaging information using a unique or dedicated focus scan profile to optimize and balance the image quality between the focused and out-of-focus regions, depending on column position and on scanned object orientation, for example.

A technical effect of at least one embodiment includes improved image quality. A technical effect of at least one embodiment includes reduced acquisition time and/or reduced injected dose.

FIG. 1 provides a schematic view of a nuclear medicine (NM) multi-head imaging system 100 in accordance with various embodiments. Generally, the imaging system 100 is configured to acquire imaging information (e.g., photon counts) from an object to be imaged (e.g., a human patient) that has been administered a radiopharmaceutical. The depicted imaging system 100 includes a gantry 110 and a processing unit 120.

The gantry 110 defines a bore 112. The bore 112 is configured to accept an object to be imaged (e.g., a human patient or portion thereof). As seen in FIG. 1, plural detector units 115 are mounted to the gantry 110. In the illustrated embodiment, each detector unit 115 includes an arm 114 and a head 116. The arm 114 is configured to articulate the head 116 radially toward and/or away from a center of the bore 112 (and/or in other directions), and the head 116 includes at least one detector, with the head 116 disposed at a radially inward end of the arm 114 and configured to pivot to provide a range of positions from which imaging information is acquired.

The detector of the head 116, for example, may be a semiconductor detector. For example, a semiconductor detector various embodiments may be constructed using different materials, such as semiconductor materials, including Cadmium Zinc Telluride (CdZnTe), often referred to as CZT, Cadmium Telluride (CdTe), and Silicon (Si), among others. The detector may be configured for use with, for example, nuclear medicine (NM) imaging systems, positron emission tomography (PET) imaging systems, and/or single photon emission computed tomography (SPECT) imaging systems.

In various embodiments, the detector may include an array of pixelated anodes, and may generate different signals depending on the location of where a photon is absorbed in the volume of the detector under a surface if the detector. The absorption of photons from certain voxels corresponding to particular pixelated anodes results in charges generated that may be counted. The counts may be correlated to particular locations and used to reconstruct an image.

Figure 2:
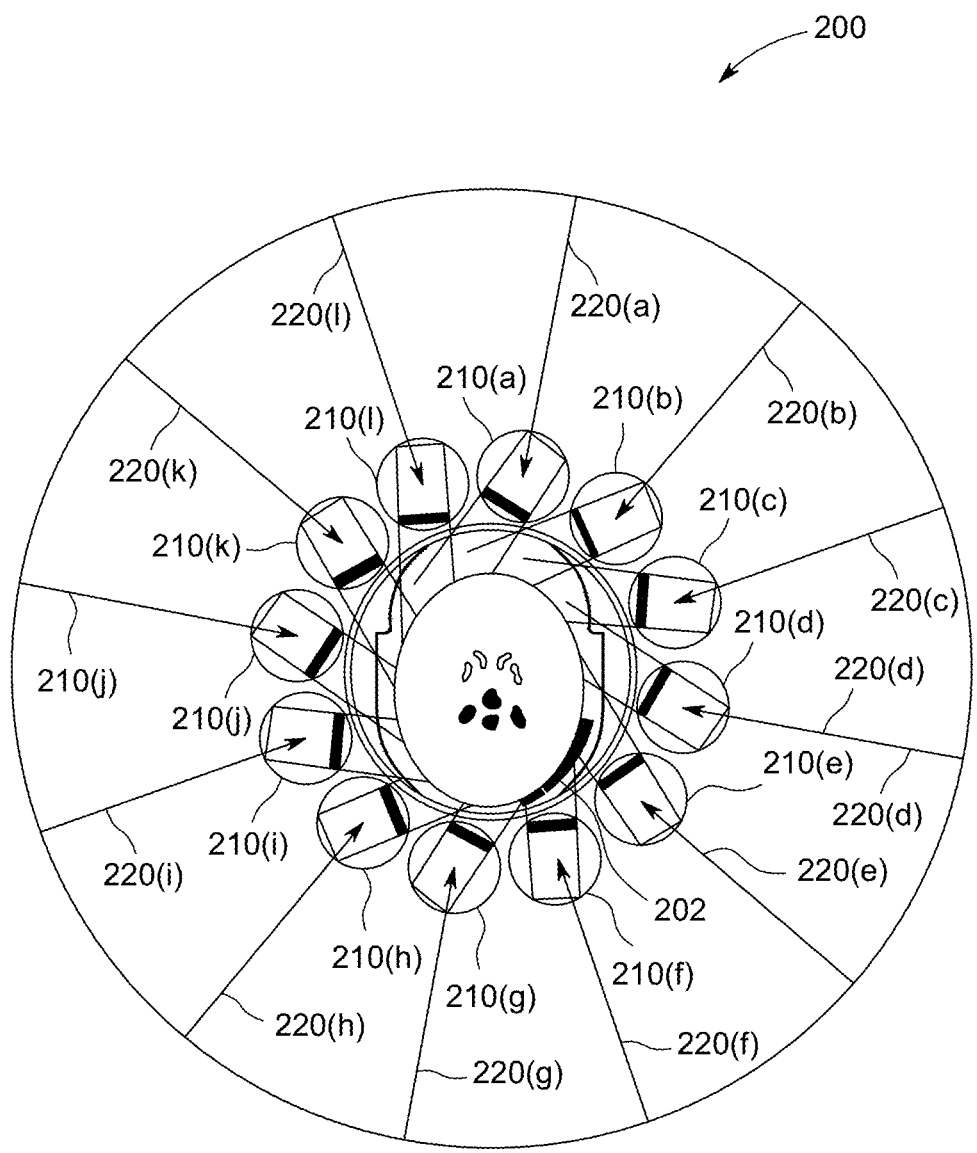
FIG. 2 provides a schematic view of a detector arrangement according to an embodiment.

In various embodiments, each detector unit 115 may define a corresponding view that is oriented toward the center of the bore 112. Each detector unit 115 in the illustrated embodiment is configured to acquire imaging information over a sweep range corresponding to the view of the given detector unit. FIG. 2 illustrates a detector arrangement 200 in accordance with various embodiments. The detector units of FIG. 1, for example, may be arranged in accordance with aspects of the detector arrangement 200. In some embodiments, the system 100 further includes a CT (computed tomography) detection unit 140. The CT detection unit 140 may be centered about the bore 112. Images acquired using both NM and CT by the system are accordingly naturally registered by the fact that the NM and CT detection units are positioned relative to each other in a known relationship. A patient may be imaged using both CT and NM modalities at the same imaging session, while remaining on the same bed, which may transport the patient along the common NM-CT bore 112.

As seen in FIG. 2, the detector arrangement 200 includes detector units 210(a), 210(b), 210(c), 210(d), 210(e), 210(f), 210(g), 210(h), 210(i), 210(j), 210(k), 210(l) disposed about and oriented toward (e.g., a detection or acquisition surface of the detector units, and/or the FOV (Field Of View), are oriented toward) an object 202 to be imaged in the center of a bore. Each detector unit of the illustrated embodiment defines a corresponding view that may be oriented toward the center of the bore of the detector arrangement 200 (it may be noted that because each detector unit may be configured to sweep or rotate about an axis, the FOV need not be oriented precisely toward the center of the bore, or centered about the center of the bore, at all times). The view for each detector unit 210, for example, may be aligned along a central axis of a corresponding arm (e.g., arm 114) of the detector unit 210. In the illustrated embodiment, the detector unit 210(A) defines a corresponding view 220(A), the detector unit 210(B) defines a corresponding view 220 (B), the detector unit 210(C) defines a corresponding view 220(C), and so on. The detector units 210 are configured to sweep or pivot (thus sweeping the corresponding FOV's) over a sweep range (or portion thereof) bounded on either side of a line defined by the corresponding view during acquisition of imaging information. Thus, each detector unit 210 may collect information over a range larger than a field of view defined by a stationary detector unit. It may be noted that, generally, the sweeping range over which a detector may potentially pivot may be larger than the corresponding view during acquisition. In some cameras, the sweeping range that a detector may pivot may be unlimited (e.g., the detector may pivot a full 360 degrees), while in some embodiments the sweeping range of a detector may be constrained, for example over 180 degrees (from a −90 degree position to a +90 degree position relative to a position oriented toward the center of the bore).

With continued reference to FIG. 1, the depicted processing unit 120 is configured to acquire imaging information via the detector units 115. The imaging information acquired by the processing unit 120 in various embodiments includes focused imaging information and background imaging information. The focused imaging information corresponds to a focused region, and the background imaging information corresponds to tissues surrounding the focused region. As used herein, both the focused region and surrounding tissue may be used for imaging and/or diagnostic purposes; however, the focused region may be more pertinent or useful for diagnostic purposes, and, accordingly, more imaging information is acquired for the focused region than for the surrounding tissue. An example of a focused region and surrounding tissue is shown in FIG. 3.

Figure 3:
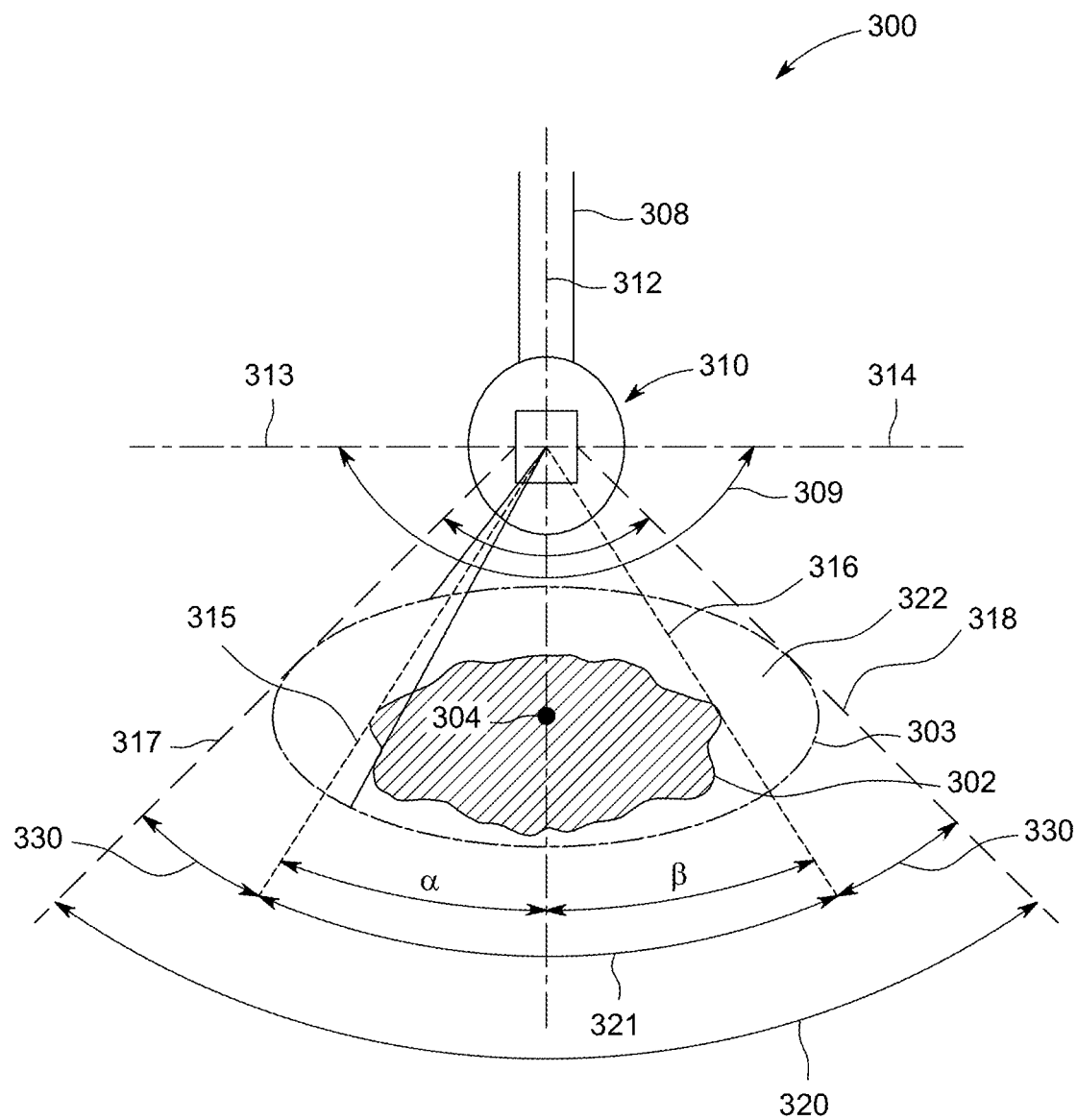
FIG. 3 depicts sweep and acquisition ranges for a detector unit according to an embodiment.

FIG. 3 depicts a focused region and surrounding tissue of an object, or a focused portion and background portion of an image. As seen in FIG. 3, the detector unit 300 includes a detector head 310 disposed at an end of a detector arm 308. In FIG. 3, only one detector unit 300 is depicted for ease and clarity of illustration. It may be noted that the detector unit 300 may be part of an arrangement of plural detector heads, such as depicted in FIGS. 1 and 2, and that the general principles discussed in connection with the detector unit 300 may be applied to one or more additional detector units of a multi-head camera imaging system. In FIG. 3, the detector unit 300 may be used to acquire imaging information (e.g., photon counts) of an object 303 having a focused region 302. In the illustrated embodiment, the focused region 302 is surrounded by surrounding tissue 322. The focused region 302, for example, may be an organ such as the heart or brain (or portion thereof), and may have a substantially larger uptake of an administered radiopharmaceutical than surrounding tissue 322 of the object 303. For example, in some embodiments, the focused region 302 is the striata of the brain, and the surrounding tissue 322 includes other portions of the brain. A ratio of detected activity between the striata and other portions of the brain may be used in analyzing whether or not a patient has Parkinson's disease. A central axis 312 of the detector unit 300 passes through a center 304 of the focused region 302 (which is disposed at the center of a bore in the illustrated embodiment). It may be noted that in various embodiments the central axis or center view of the detector need not necessarily pass through the focus center or through the focused region. The central axis 312, for example, may correspond to a line along the view corresponding to the detector unit 300 when the detector unit 300 is at a midpoint of a range of coverage of the detector unit 300, and/or may be aligned with a central axis of the detector arm 308 to which the detector head 310 is attached.

In the illustrated embodiment, the detector unit 300 is depicted as aligned with the central axis 312, and may be rotated, pivoted or swept over a sweep range 309 between a first limit 313 and a second limit 314. In the illustrated embodiment, the first limit 313 and the second limit 314 define a sweep range 309 (or maximum range of coverage) of 180 degrees. In other embodiments, the sweep range 309 and/or relative positions of the first limit 313 and second limit 314 may vary from the depicted arrangement. It may be noted that the sweep range 309 provides more coverage than is required to collect imaging information of the focused region 302 and the surrounding tissue 322. Thus, if the detector unit 300 is swept over the sweep range 309 during a duration of an imaging acquisition, information that may be not be useful for diagnostic purposes (e.g., information towards the ends of the sweep range 309 that does not include information from either the focused region 302 or the surrounding tissue 322) may be collected. The time used to collect the information that is not useful for diagnostic purposes may be more efficiently spent collecting additional information from the focused region 302 and/or the surrounding tissue 322. Accordingly, in the illustrated embodiment, the detector unit 310 may be controlled (e.g., by processing unit 120) to be swept or pivoted over an acquisition range 320 (e.g., a range including the focused region 302 and surrounding tissue 322) instead of over the entire sweep range 309 during acquisition of imaging information.

As seen in FIG. 3, the acquisition range 320 generally corresponds to edges of the surrounding tissue 322, and is bounded by a first boundary 317 and a second boundary 318. A focused range 321 is defined within the acquisition range 320 and corresponds to edges of the focused region 302. The focused range 321 is bounded by a first boundary 315 and a second boundary 316. Generally, more imaging information is acquired over the focused range 321 than over the background portions 330 of the acquisition range 320 which include the surrounding tissue 322 but not the focused region 302. Generally, more time is spent acquiring information over the focused range 321 than over the background portions 330. For example, the detector 310 may be swept at a higher sweep rate over the background portions 330 when acquiring the background imaging information than over the focused range 321 when acquiring the focused imaging information. The first boundary 315 is located at an angle α in clockwise direction from the central axis 312 (and, in the illustrated embodiment, from the center 304). The second boundary 316 is located at an angle β in a counterclockwise direction from the central axis 312 (and, in the illustrated embodiment, from the center 304).

It may be noted the boundaries may not necessarily correspond to a central axis or portion of a field of view of the detector unit, but may correspond to an edge or other portion of the field of view. Further, the acquisition range 320 may be configured in various embodiments to include more or less surrounding tissue beyond the focused region. Further, the acquisition range 320 may include an amount of background or surrounding tissue for a first phase of an acquisition period and omit background or surrounding tissue for a second phase; or omit the acquisition of surrounding tissue altogether (for one or several detector units comprising the system).

Figure 4:
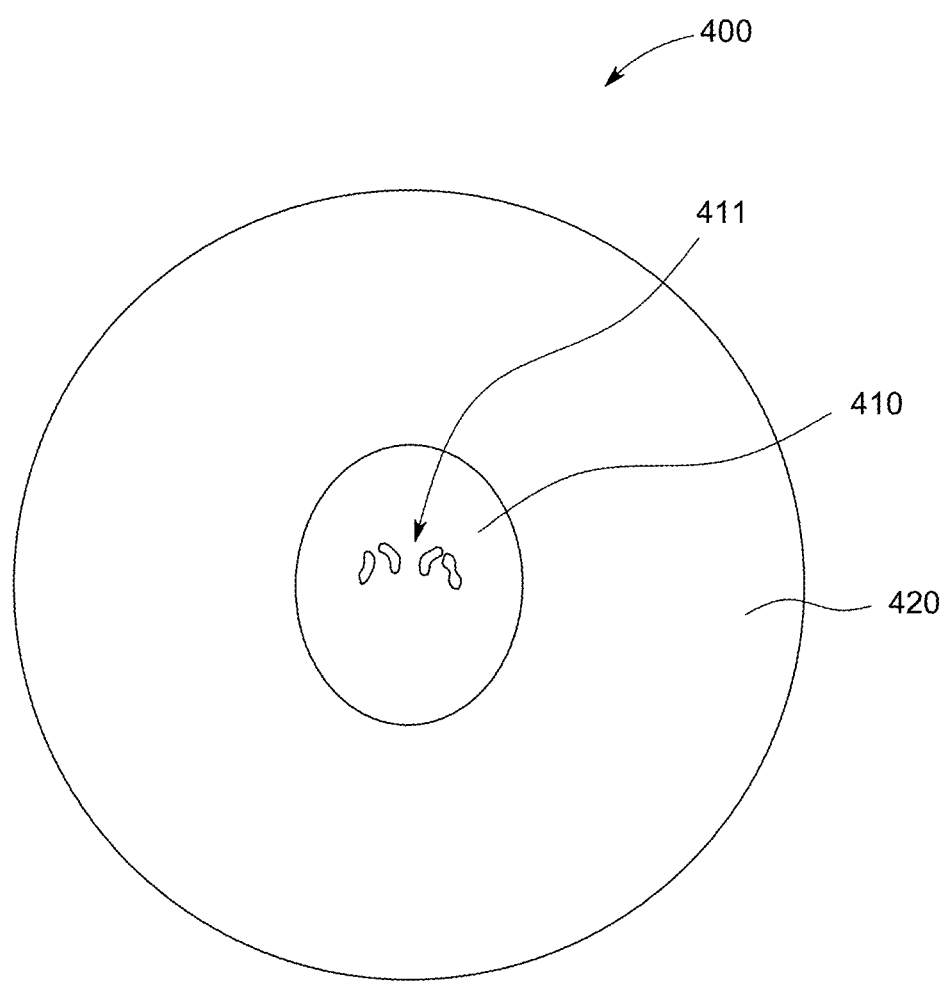
FIG. 4 provides a schematic view of an image having regions that have been reconstructed using different techniques in accordance with an embodiment.

The depicted processing unit 120 is also configured to reconstruct an image using the focused imaging information and the background information. In various embodiments, the processing unit 120 uses a first reconstruction technique for the focused imaging information (e.g., information corresponding to the focused region 302 acquired over the focused range 321) and a different, second reconstruction technique for the background imaging information (e.g., information corresponding to the surrounding tissue 322 that has been acquired over portions 330 of the acquisition range 320). FIG. 4 provides a schematic view of an image 400 having regions that have been reconstructed using different techniques. As seen in FIG. 4, the image 400 includes a focused region 410, and a background region 420. In the depicted example, the focused region 410 includes the striata 411 and the background region 420 includes surrounding portions of the brain. The image 400 is reconstructed using differing techniques—a first technique is used to reconstruct the focused region 410 (using the focused imaging information), and a second technique is used to reconstruct the background region 420 (using the background imaging information).

Put another way, reconstruction techniques may be applied regionally or locally—with a first technique (e.g., method and/or parameter) or group of techniques used for the focused imaging information (e.g., acquired over focused range 321) and a second technique (or group of techniques) used for the background imaging information (e.g., acquired over portions 330). For example, because there is less background imaging information, noise may have a more prevalent effect in the background region than the focused region. Accordingly, a reconstruction technique that more aggressively addresses noise may be employed when reconstructing the background imaging information.

For example, voxel space filtering may differ between the focused imaging information and the background imaging information. Filters (and/or other de-noising methods) may be applied differently by regions for the reconstructed object volume. For example, a first filter or de-noising method may be applied to the focused imaging information and a second filter or de-noising method may be applied to the background imaging information when using both the focused imaging information and the background imaging information together to generate an image. It may be noted such application of filtering applies to post-reconstruction filters (e.g., filters applied once after reconstruction is completed) as well as intermediate filters (e.g., filters applied during reconstruction). For example, any of the filters may be applied initially after a given number of iterations, and/or repeated after a given number of iterations during a reconstruction.

Another example of reconstruction techniques that may be varied locally or regionally includes projection (pixel space) filtering. In various embodiments, projection filtering may differ between the focused imaging information and the background imaging information. Filters (and/or other de-noising methods) may be applied on projections according to the location (e.g., within a focused range, within a background range) according to the location at which the projections are overlooking an object or portion thereof being imaged. It may be noted such application of filtering may be performed prior to reconstruction (e.g., pre-filtering an original acquisition projection or projections) or during reconstruction. For example, such filters may be applied initially after a given number of iterations, and/or repeated after a given number of iterations during a reconstruction.

As one more example, algorithms employed may vary locally or regionally. For example, algorithm step-size iteration updates may differ between the focused imaging information and the background imaging information. Different step-sizes may be defined in different regions of the object (e.g., a first step-size in a focused range and a second, different step-size in a background range) to force different rates of algorithm convergence for the regions. Such different rates of algorithm convergence in various embodiments leads to differences in reconstructed detail and/or image noise levels, which may be beneficial to overall image quality.

As yet one more example, a different number of reconstruction iterations may be employed for focused imaging information relative to background imaging information. It may be noted that the results of the different iterations steps will differ between regions in reconstructed detail level and noise qualities, which may be beneficial to overall image quality.

In some embodiments, the first reconstruction technique (used with the focused imaging information) is configured as or includes a first regularization technique employing a first regularization weight parameter, and the second reconstruction technique is configured as or includes a second regularization technique employing a different, second regularization weight parameter. In some embodiments, the first and second regularization technique may be generally similar and have the same form, and differ by virtue of the different first and second regularization weight parameters. In other embodiments, the first and second regularization techniques may have different formats.

Various embodiments may be understood as employing regularized reconstruction with non-uniform regularization (or penalty) weights. Accordingly a first regularization weight parameter may be different (e.g., higher or lower) than a second regularization weight parameter. Generally, regularized reconstruction allows control of a balance between uniformity (or noise) and resolution/contrast using a weight parameter β. For example, a relatively large β may provide a high level of smoothing, and increase uniformity, but provide a relatively lower level of resolution/contrast. Accordingly, a relatively large β may prove useful in connection with imaging information that has relatively high noise levels (or low counts). In contrast, a relatively low β provides a lower level of smoothing and decreased uniformity, but provides a relatively higher level of resolution/contrast. Accordingly, a relatively low β may prove useful for imaging information with low noise levels (or high counts). Conventionally, a fixed value of β has been used; however such a fixed β may be disadvantageous for use in connection with focused regions having more information and background regions having less information as discussed in connection with various embodiments herein. Accordingly, in various embodiments, localized values of β are employed. For example, a first $β_1$ having a relatively lower value may be used for the focused imaging information, and a second $β_2$ having a relatively higher value may be used for the background imaging information. In some embodiments $β_2$ may be ten times or more larger than $β_1$. For example, $β_2$ may be 0.02 and $β_1$ may be 0.002. It may be noted that, in some embodiments, beta values may be adaptive (e.g., per scan) instead of being pre-determined. For example, $β_1$ and/or $β_2$ values may be determined according to the amount of acquisition time spent in the focus and/or background regions, or as another example, according to the number of photon counts collected, or as still another example, according to a combination of time and counts.

Generally, a smaller $β_1$ may be used in connection with the focused imaging information to provide relatively high contrast and/or resolution for the focused region for which a relatively larger amount of information is available, while the larger $β_2$ may be used in connection with the background imaging information to provide improved smoothness or improved noise performance for the background region for which a relatively smaller amount of information is available.

In some embodiments, the second reconstruction technique (employed in connection with the background imaging information) includes additional iterative reconstructions relative to the first reconstruction technique (employed in connection with the focused imaging information). For example, in various embodiments, the processing unit 120 is configured to acquire first original projections of the focused imaging data and second original projections of the background imaging data during an imaging acquisition; to perform initial iterations using the background imaging data to perform an initial background reconstruction; to perform a forward projection on the initial background reconstruction to provide modified background projections; to combine the modified background projections with the original projections of the focused imaging data to provide combined projections; and to perform final iterations on the combined projections to provide a final reconstruction. It may be noted that the order in various embodiments could be vice versa of what is discussed above. Namely, background projections may be acquired before focused projections (see also, e.g., FIG. 3). The order may also be different for different detector units.

Figure 5:
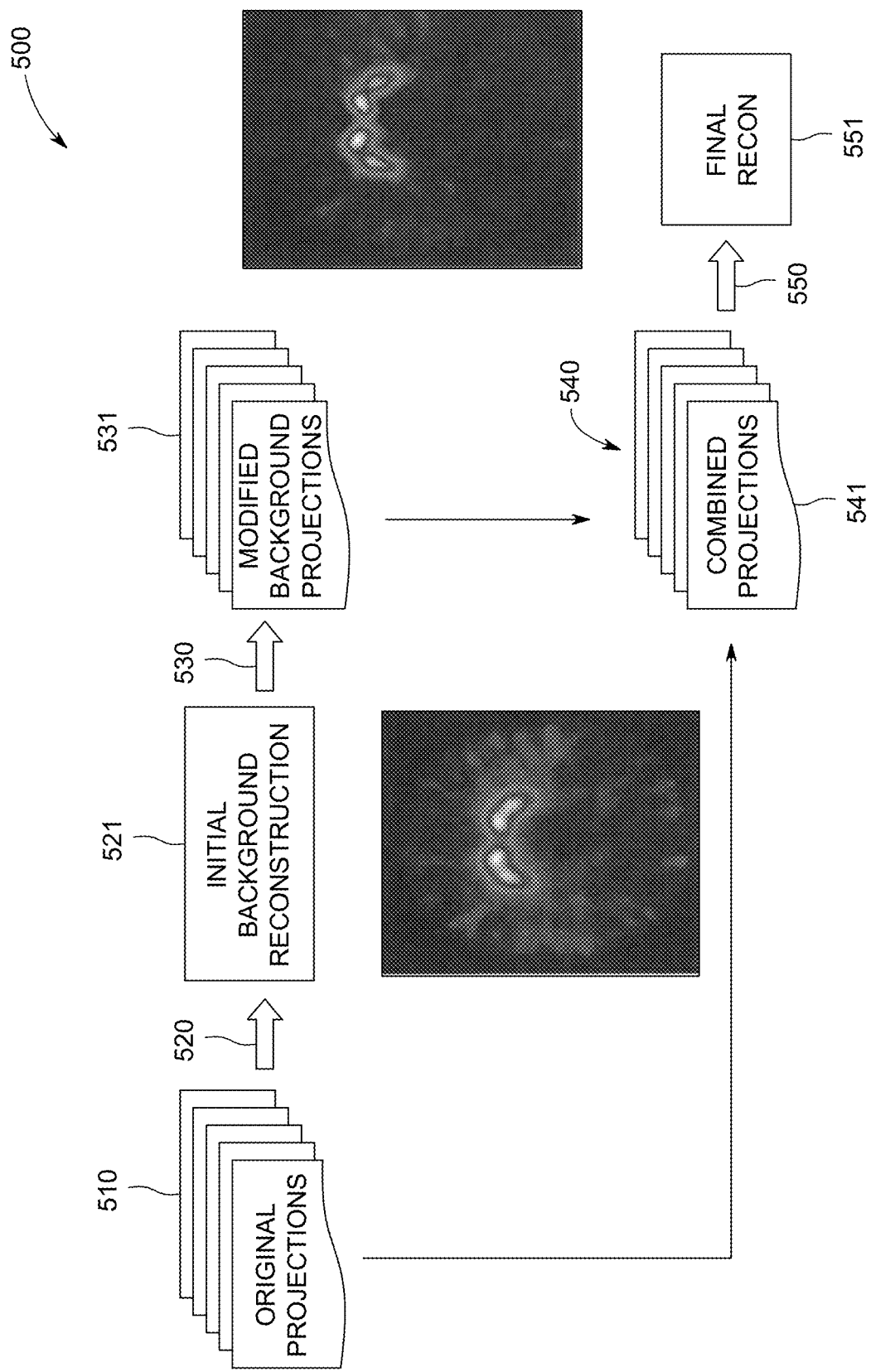
FIG. 5 provides a schematic view of a process flow according to an embodiment.

For example, FIG. 5 provides a schematic view of a process flow 500 using additional iterative reconstructions for the background imaging information relative to the focused imaging information. At 510, original projections are acquired. For example the original projections may be acquired using plural detector heads having corresponding sweep ranges as discussed herein. Some of the original projections are for focused regions (for which relatively more imaging information is acquired), while others of the original projections are for background regions (for which relatively less imaging information is acquired). In the illustrated embodiment, the original projections are divided into 2 groups—background projections and focused projections. At 520, the background projections (with or without the focused projections) are reconstructed as part of an initial background reconstruction 521. For example, both focused and background projection may be used for an initial reconstruction, with a forward projection step (see, e.g., step 530) utilizing only the back range. The background regions may be reconstructed using a relatively low number of iterations for an iterative reconstruction process. For example, less than 100 iterations may be used to reconstruct the initial background reconstruction. In some embodiments, 10-20 iterations are used to reconstruct the initial background reconstruction. At 530, the initial background reconstruction 521 is forward projected (e.g., using a technique simulating the measurement process of detectors) to provide modified background projections 531.

Next, at 540, the modified background projections are combined with the original focused projections acquired at 510 (and previously separated from the original background projections before the initial background reconstruction) to provide combined projections 541. It may be noted that the projections need not necessarily be separated for use in the original, low iteration reconstruction. It may further be noted that to help ensure a smooth transition between the original projections and the re-projected projections, a weighting between the acquired (measured) projection and the calculated projections (the results of the forward projections) may be employed. At 550, final iterations are performed on the combined projections to provide a final reconstruction 551. The final reconstruction process may use a relatively high number of iterations. For example, more than 100 iterations may be used to reconstruct the final reconstruction. In some embodiments, 300-400 iterations are used to reconstruct the final reconstruction of the combined projections.

Generally, in iterative reconstruction algorithms, as the algorithm approaches convergence (i.e., as iteration count increases), the resolution/contrast is improved, but noise from projections used with the iterative process is intensified and acts to degrade image quality (e.g., by decreasing uniformity). Because the background (or out of focus) imaging information has a relatively short acquisition time, the noise level of the raw background imaging information is relatively high. Accordingly, in various embodiments, original background imaging information with relatively high noise levels is replaced with lower noise data of the same area. This is accomplished using re-projected data from an initial reconstruction of the background imaging information. The initial reconstruction uses the original background imaging information but stops after a relatively low number of iterations, thereby providing a relatively low noise level in the initial reconstruction. The re-projected background projections are combined with originally acquired projections from the focused regions, and then a second reconstruction with a relatively high number of iterations is performed. Accordingly, high resolution and/or contrast for the focused region along with reasonable uniformity in the background regions is provided in various embodiments.

Various embodiments discussed above related to, for example, the use of different reconstruction techniques in connection with corresponding different portions of imaging information (e.g., focused imaging information and background (or out-of-focus) imaging information). Additionally or alternatively, in various embodiments, non-uniform focus scan patterns (e.g., different scan patterns for different detectors) may be employed to improve image quality for scanning procedures in which both focused imaging information and background (or out-of-focus) imaging information is acquired. For example, in some embodiments, the processing unit 120 is configured to independently determine, for each detector unit, a percentage of focused time for acquiring the focused imaging information for the focused imaging information, and percentage of background time for acquiring the background imaging information.

For example, if a uniform focus scan pattern is employed, a common focus criterion or profile may be applied to all columns (e.g., 80% of acquisition time spent for acquiring focused imaging information and 20% of acquisition time spend for acquiring backing imaging information). However, such an approach may not optimally leverage the quality of focused and/or background imaging information available for each particular detector. Accordingly, in some embodiments, different focus criteria or a different focus profile is defined independently for detectors (e.g., a different focus criteria or profile for each detector). The focus criteria or profile is determined independently for each detector by the processing unit 120, for example, to improve out-of-focus or background image quality without noticeable degradation of the focused region image quality.

Figure 6:
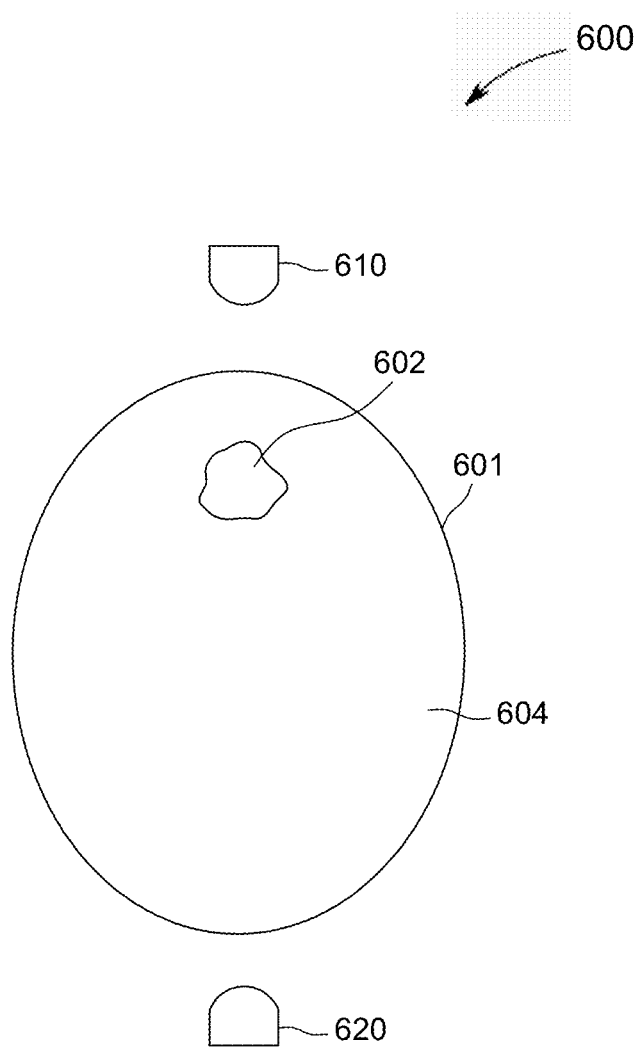
FIG. 6 illustrates an example of a detector system, according to an embodiment.

FIG. 6 illustrates an example of a detector system 600 that includes detectors for which focus criteria (e.g., percentages of time spent acquiring focused imaging information versus time spent acquiring backing imaging information) may be independently determined. Only two detectors are shown for ease of illustration; however, it may be noted that more detectors may be employed in various embodiments. An object 601 has a focused region 602 and a background region 604. The system 600 is configured to acquire more imaging information for the focused region 602 than for the background region 604.

A first detector 610 is positioned relatively close to the focused region 602. The first detector 610 acquires imaging information at a relatively higher resolution for the focused region 602 than a detector positioned farther away from the focused region 602. Accordingly, the first detector 610 has a relatively high contribution to the focused region 602, and is configured in the illustrated embodiment to spend more time acquiring focused imaging information for the focused region 602 relative to other detectors that are not positioned as favorably with respect to the focused region 602. For example, if the system 600 as a whole has a target of 80% focused imaging information and 20% background imaging information, the first detector 610 spends more than 80% of its time acquiring focused imaging information (e.g., 90%) and less than 20% of its time acquiring background imaging information (e.g., 10%).

As seen in FIG. 6, a second detector 620 is positioned relatively far from the focused region 602. Accordingly the second detector 620 "sees" the focused region 602 worse than the first detector 610 does, for example due to collimator position as well as a reduced number of photon counts (due to increased attenuation relative to the first detector 610). The second detector 620 acquires imaging information at a relatively lower resolution for the focused region 602 than a detector positioned closer to the focused region 602 (e.g., first detector 610). Accordingly, in the illustrated embodiment the second detector 620 is configured to spend a relatively larger amount of time acquiring background imaging information to improve the background image quality. Use of the second detector 620 to acquire more background information in the illustrated embodiment will not appreciably downgrade the focused region image quality as the resolution and counts for the focused region 602 available via the second detector 620 are relatively low due to the distance and attenuation. For example, if the system 600 as a whole has a target of 80% focused imaging information and 20% background imaging information, the second detector 620 spends less than 80% of its time acquiring focused imaging information (e.g., 40%) and more than 20% of its time acquiring background imaging information (e.g., 60%). The particular percentages for the example discussed in connection with FIG. 6 are provided by way of example for illustrative purposes. Other percentages may be used in other embodiments. For example, in some embodiments, the first detector 610 (and/or other detector) may spend 100% of its acquisition time acquiring focused imaging information, and/or the second detector 620 (and/or other detector) may spend 100% of its acquisition time acquiring background imaging information.

Generally, various factors may be considered when determining what percentages of time a given detector will spend acquiring focused imaging information and background imaging information. For example, the scan pattern may be determined individually for each detector based on the particular detector's proximity to the focused region, the relative angular span of the focused region compared to a total detector angular field of view for the particular detector, and/or the anticipated attenuation and scatter qualities of the object between the focused region and the particular detector.

Returning to FIG. 1, in various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, FPGA's, ASIC's and/or computers, which may be integrated in a common housing or unit, or which may distributed among various units or housings (e.g., one or more aspects of the processing unit 120 may be disposed onboard one or more detector units, and one or more aspects of the processing unit 120 may be disposed in a separate physical unit or housing). The processing unit 120, for example, may determine of acquisition range boundaries for focused and background regions (e.g., based on a scout scan and/or anatomical models), control the detector heads to acquire desired amounts of focused and background information (e.g., 80% of acquisition time on focused region, or, as another example, an independently determined percentage of acquisition time on the focused region for each detector), and reconstruct an image as discussed herein. It may be noted that operations performed by the processing unit 120 (e.g., operations corresponding to process flows or methods discussed herein, or aspects thereof) may be sufficiently complex that the operations may not be performed by a human being within a reasonable time period. For example, identifying boundaries of acquisition ranges, providing control signals to detector units, reconstructing images, or the like may rely on or utilize computations that may not be completed by a person within a reasonable time period.

In the illustrated embodiment, the processing unit 120 includes a reconstruction module 122, a control module 124, and a memory 130. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

In the illustrated embodiment, the depicted reconstruction module 122 is configured to reconstruct an image. For example, the reconstruction module 122 in various embodiments used different reconstruction techniques for different portions of an image as discussed herein.

The depicted control module 124 is configured to control the detector heads 116 to sweep over corresponding acquisition ranges to acquiring focused imaging information and background imaging information as discussed herein. For example, the control module 124 may control a detector head to sweep at a slower speed over a focused range than over a background range. It may be noted that, in various embodiments, aspects of the control module 124 may be distributed among detector units 115. For example, each detector unit may have a dedicated control module disposed in the head 116 of the detector unit 115.

The memory 130 may include one or more computer readable storage media. The memory 130, for example, may store information describing previously determined boundaries of acquisition ranges, parameters to be utilized during performance of a scan (e.g., speed of rotation for focused range, speed of rotation for background range, time or total count value over which an acquisition is to be performed), parameters to be used for reconstruction (e.g., regularization weight parameter, number of iterations) or the like. Further, the process flows and/or flowcharts discussed herein (or aspects thereof) may represent one or more sets of instructions that are stored in the memory 130 for direction of operations of the imaging system 100.

It may be noted that while the processing unit 120 is depicted schematically in FIG. 1 as separate from the detector units 115, in various embodiments, one or more aspects of the processing unit 120 may be shared with the detector units 115, associated with the detector units 115, and/or disposed onboard the detector units 115. For example, in some embodiments, at least a portion of the processing unit 120 is integrated with at least one of the detector units 115.

Figure 7:
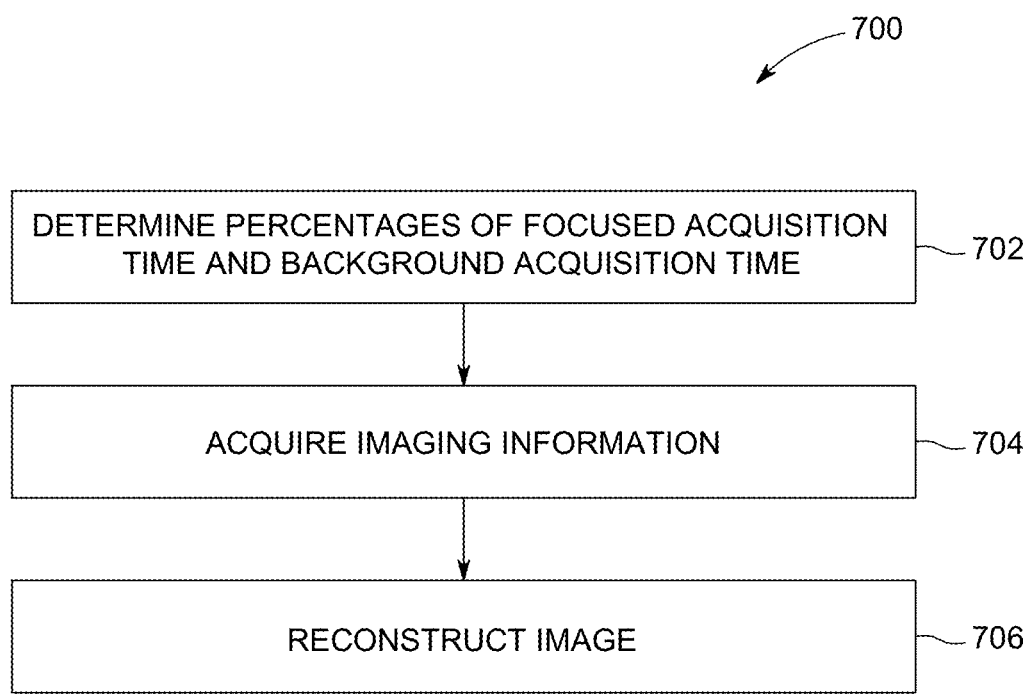
FIG. 7 shows a flowchart of a method, according to an embodiment.

FIG. 7 provides a flowchart of a method 700 for controlling detector heads of a multi-head imaging system and/or reconstructing an image using focused and non-focused (or background) imaging information acquired with detector heads of a multi-head imaging system in accordance with various embodiments. The method 700 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be able to be used as one or more algorithms to direct hardware (e.g., one or more aspects of the processing unit 120) to perform one or more operations described herein.

At 702, percentages of focused acquisition time and background acquisition time are determined. For example, one or more processors (e.g., processing unit 120) in various embodiments determines, independently for each detector unit, a percentage of focused time for acquiring focused imaging information, and a percentage of background time for acquiring background imaging information. The sweeping speed of detector heads may be controlled to achieve the desired percentages of acquired information over the focused and non-focused ranges. The percentages in various embodiments may be determined based on at least one of detector proximity to the focused region, relative angular span of the focused region relative to total detector angular field of view, or anticipated attenuation qualities in a detector field of view.

At 704, imaging information is acquired. The imaging information in various embodiments is acquired using plural detector units, with each detector unit defining a detector view and having a sweep range (see, e.g., FIGS. 1-3 and related discussion). The imaging information includes focused imaging information that corresponds to a focused region and background information corresponding to surrounding tissue of the focused region. The focused region is a region of relatively higher diagnostic interest or usefulness for which a relatively higher amount of imaging information is acquired, while the background region is of relatively lower diagnostic interest or usefulness for which a relatively lower amount of imaging information is acquired. For example, the focused region in some embodiments includes the striata, and the background region includes other portions of the brain. In various embodiments, to acquire more imaging information for the focused region than for the background region, detector units are swept at a higher sweep rate when acquiring the background imaging information than when acquiring the focused imaging information. Accordingly, the detector heads spend more time acquiring the focused imaging information than the background imaging information. It may be noted that as the detector heads sweep back and forth, a percentage of time over the total swept range is spend acquiring focused imaging information and a percentage of time is spent acquiring background. In some embodiments the percentages may be determined independently for each detector, for example at 702. In other embodiments, the percentages may be uniform across all detectors.

At 706, an image is reconstructed. In various embodiments, the image is reconstructed using the focused imaging information and the background information. The focused imaging information is used with a first reconstruction technique, and the background imaging information is used with a different, second reconstruction technique. As used herein different techniques may be distinguished from each other based on values of one or more parameters (e.g., using a generally similar methodology for focused and background imaging information, but using different values for one or more parameters, such as a regularization weight parameter), different methodologies, and/or different numbers of steps and/or iterations.

In some embodiments the first reconstruction technique includes a first regularization technique employing a first regularization weight parameter. Similarly, the second reconstruction technique includes a second regularization technique that employs a different, second regularization weight parameter. Thus, while regularization techniques may be employed in reconstructing both the focused imaging information and the background imaging information, different weight (or penalty) parameters may be used for the focused imaging information and the background imaging information. For example, the first regularization weight parameter (used with the focused imaging information) may be less than the second regularization weight parameter (used with the background imaging information). In some embodiments, the value of the second regularization weight parameter may be ten times or more the value of the first regularization weight parameter.

As another example, the second reconstruction technique (used with the background information) may include extra additional iterative reconstructions relative to the first reconstruction technique. For example, the background imaging information and focused imaging information may be utilized as discussed in connection with FIG. 5 herein.

Figure 8:
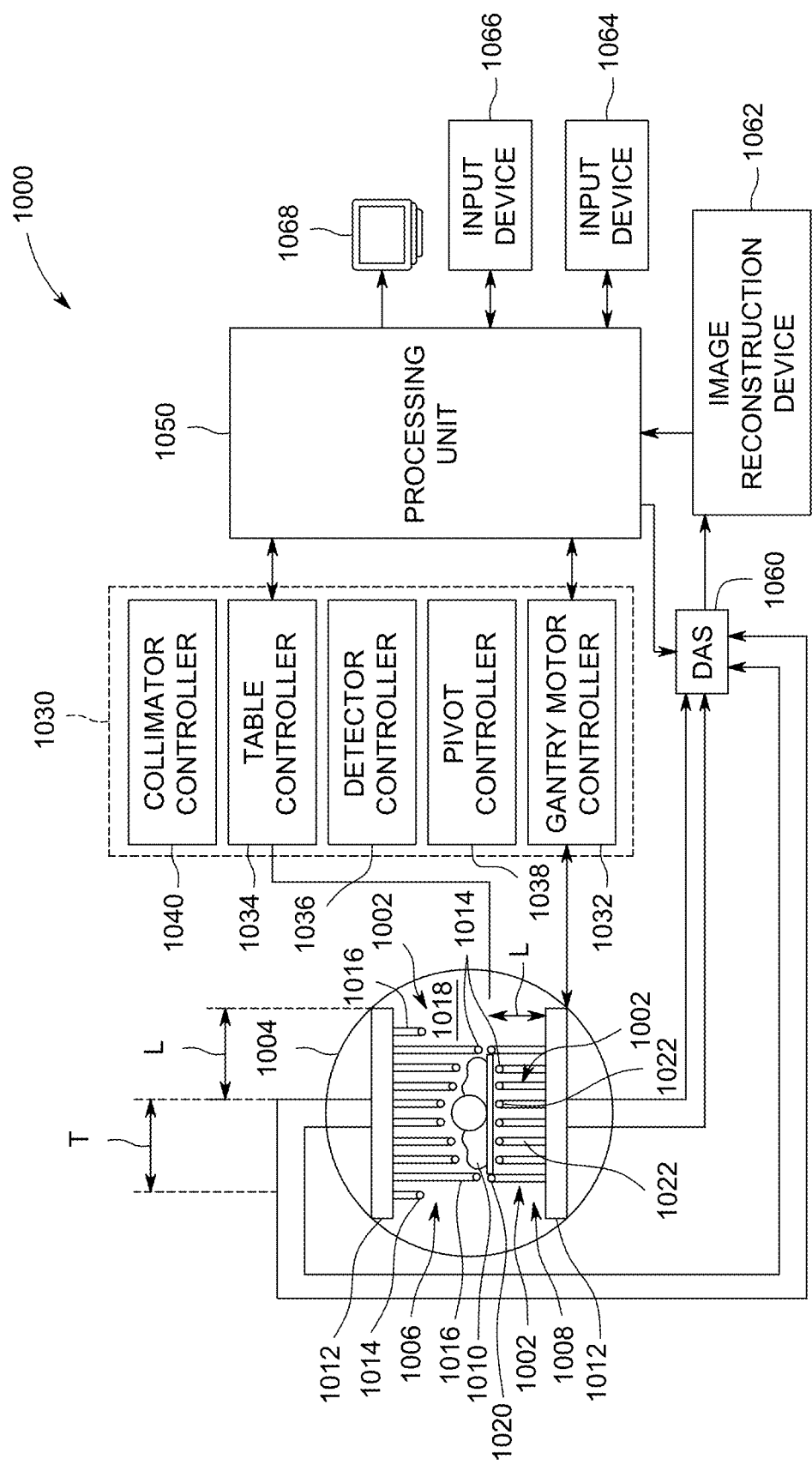
FIG. 8 shows a schematic view of an imaging system, according to an embodiment.

Embodiments described herein may be implemented in medical imaging systems, such as, for example, SPECT, SPECT-CT, PET and PET-CT. Various methods and/or systems (and/or aspects thereof) described herein may be implemented using a medical imaging system. For example, FIG. 8 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 8 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 8. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 8). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels (pixelated anodes). In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 8 are depicted for ease of illustration as single collimators in each detector head. Optionally, for embodiments employing one or more parallel-hole collimators, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 8 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

It should be noted that the particular arrangement of components (e.g., the number, types, placement, or the like) of the illustrated embodiments may be modified in various alternate embodiments, and/or one or more aspects of illustrated embodiments may be combined with one or more aspects of other illustrated embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A nuclear medicine (NM) multi-head imaging system comprising:
   a gantry defining a bore configured to accept an object to be imaged;
   plural detector units mounted to the gantry, each detector unit defining a detector unit position and corresponding view oriented toward a center of the bore, each detector unit configured to acquire imaging information over a sweep range corresponding to the corresponding view, wherein the detector units are configured to be swept independently of gantry rotation; and at least one processor operably coupled to at least one of the detector units, the at least one processor configured to:
acquire, via the at least one of the detector units, imaging information, the imaging information comprising focused imaging information corresponding to a focused region of the object to be imaged and background imaging information corresponding to surrounding tissue of the object to be imaged of the focused region; and
reconstruct, after acquiring the imaging information, an image using the focused imaging information and the backgound imaging information using a first reconstruction technique for the focused imaging information acquired via the at least one of the detector units and a different, second reconstruction technique for the background imaging information acquired via the at least one of the detector units, wherein the second reconstruction technique comprises additional iterative reconstructions relative to the first reconstruction technique, wherein the processor is configured to:
acquire first original projections of the focused imaging data and second original projections of the background imaging data during an imaging acquisition;
perform initial iterations using at least the background imaging data to perform an initial background reconstruction;
perform a forward projection on the initial background reconstruction to provide modified background projections;
combine the modified background projections with the original projections of the focused imaging data to provide combined projections; and
perform final iterations on the combined projections to provide a final reconstruction.

2. The system of claim 1, wherein the at least one processor is configured to sweep each detector unit at a higher sweep rate when acquiring the background imaging information than when acquiring the focused imaging information.

3. The system of claim 1, wherein the first reconstruction technique comprises a first regularization technique employing a first regularization weight parameter, and wherein the second reconstruction technique comprises a second. regularization technique employing a different, second regularization weight parameter.

4. The system of claim 3, wherein the first regularization weight parameter is different than the second regularization weight parameter.

5. The system of claim 4, wherein the second regularization weight parameter is at least ten times the first regularization weight parameter.

6. The system of claim 1, wherein the initial iterations number less than 100, and the final iterations number more than 100.

7. The system of claim 1, wherein the processor is configured to independently determine, for each detector unit, a percentage of focused time for acquiring information for the focused imaging information, and a percentage of background time for acquiring information for the background imaging information.

8. A method comprising:
acquiring, via plural detector units each defining a detector view and having a sweep range, imaging information comprising focused imaging information corresponding to a focused region of the object to he imaged and background imaging information corresponding to surrounding tissue of the object to be imaged of the focused region, wherein the detector units are swept independently of gantry rotation; and
reconstructing an image, after acquiring the imaging information, using the focused imaging information and the background imaging information using a first reconstruction technique for the focused imaging information acquired via the detector units and a different, second reconstruction technique for the background imaging information acquired via the detector units, wherein the second reconstruction technique comprises additional iterative reconstructions relative to the first reconstruction technique, the method comprising:
acquiring first original projections of the focused imaging data and second original projections of the background imaging data during an imaging acquisition;
performing initial iterations using at least the background imaging data to perform an initial background reconstruction;
performing a forward projection on the initial background reconstruction to provide modified background projections;
combining the modified background projections with the original projections of the focused imaging data to provide combined projections; and
performing final iterations on the combined projections to provide a final reconstruction.

9. The method of claim 8, acquiring the imaging information comprises sweeping each detector unit at a higher sweep rate when acquiring the background imaging information than when acquiring the focused imaging information.

10. The method of claim 8, wherein the first reconstruction technique comprises a first regularization technique employing a first regularization weight parameter, and wherein the second reconstruction technique comprises a second regularization technique employing a different, second regularization weight parameter.

11. The method of claim 10, wherein the first regularization weight parameter is lower than the second regularization weight parameter.

12. The method of claim 11, wherein the second regularization weight parameter is at least ten times the first regularization weight parameter.

13. The method of claim 8, wherein the initial iterations number less than 100, and the final iterations number more than 100.

14. The method of claim 8, further comprising:
independently determining, for each detector unit, a percentage of focused time for acquiring the focused imaging information, and a percentage of background time for acquiring the background imaging information; and
acquiring the imaging information using the determined percentages of focused time and background time.

* * * * *